(12) United States Patent
Böbst et al.

(10) Patent No.: US 8,092,425 B2
(45) Date of Patent: Jan. 10, 2012

(54) SYRINGE CYLINDER

(75) Inventors: Benjamin Böbst, Mittelbiberach (DE); Dirk Peters, Ravenburg (DE); Frank Boettger, Ravensburg (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 546 days.

(21) Appl. No.: 12/226,465

(22) PCT Filed: Apr. 19, 2007

(86) PCT No.: PCT/EP2007/003429
§ 371 (c)(1),
(2), (4) Date: Oct. 17, 2008

(87) PCT Pub. No.: WO2007/121915
PCT Pub. Date: Nov. 1, 2007

(65) Prior Publication Data
US 2009/0082737 A1     Mar. 26, 2009

(30) Foreign Application Priority Data
Apr. 21, 2006 (DE) .................. 10 2006 018 651

(51) Int. Cl.
*A61M 5/00* (2006.01)
*A61M 5/315* (2006.01)
(52) U.S. Cl. .................. 604/111; 604/260; 604/220
(58) Field of Classification Search ............ 604/97.03, 604/100.01–100.03, 111, 186, 187, 207, 604/218, 246, 260, 220, 221
See application file for complete search history.

(56) References Cited

U.S. PATENT DOCUMENTS

| | | | |
|---|---|---|---|
| 3,941,129 A * | 3/1976 | Pleznac | 604/111 |
| 4,252,118 A | 2/1981 | Richard et al. | |
| 4,392,852 A * | 7/1983 | Butterfield | 604/111 |
| 5,338,311 A | 8/1994 | Mahurkar | |
| 5,586,975 A | 12/1996 | Tanaka et al. | |
| 5,688,252 A | 11/1997 | Matsuda et al. | |
| 5,720,731 A | 2/1998 | Aramata et al. | |
| 6,090,081 A | 7/2000 | Sudo et al. | |

FOREIGN PATENT DOCUMENTS

| | | |
|---|---|---|
| DE | 27 17 830 A1 | 11/1977 |
| DE | 196 47 694 C1 | 6/1998 |
| DE | 698 00 582 T2 | 6/2001 |
| DE | 695 26 556 T2 | 8/2002 |
| DE | 696 22 909 T2 | 12/2002 |
| DE | 694 32 458 T2 | 2/2004 |
| DE | 697 21 781 T2 | 3/2004 |
| DE | 699 18 962 T2 | 12/2004 |
| EP | 0 879611 B1 | 6/2001 |
| EP | 0 709 106 B1 | 5/2002 |
| EP | 0 737 484 B1 | 8/2002 |
| EP | 0 671 179 B1 | 4/2003 |
| EP | 0 915 740 B1 | 5/2003 |
| EP | 1 064 037 B1 | 7/2004 |
| WO | WO 98/19715 | 5/1998 |

* cited by examiner

*Primary Examiner* — Kevin C Sirmons
*Assistant Examiner* — Andrew Gilbert
(74) *Attorney, Agent, or Firm* — Harness, Dickey & Pierce, P.L.C.

(57) ABSTRACT

A syringe cylinder comprising an interior space, having a stopper that can be displaced in the interior space and delimits an active ingredient space, is proposed. The syringe cylinder is characterized by an indicator device biuniquely indicating a longitudinal movement of the stopper occurring in one direction.

10 Claims, 2 Drawing Sheets

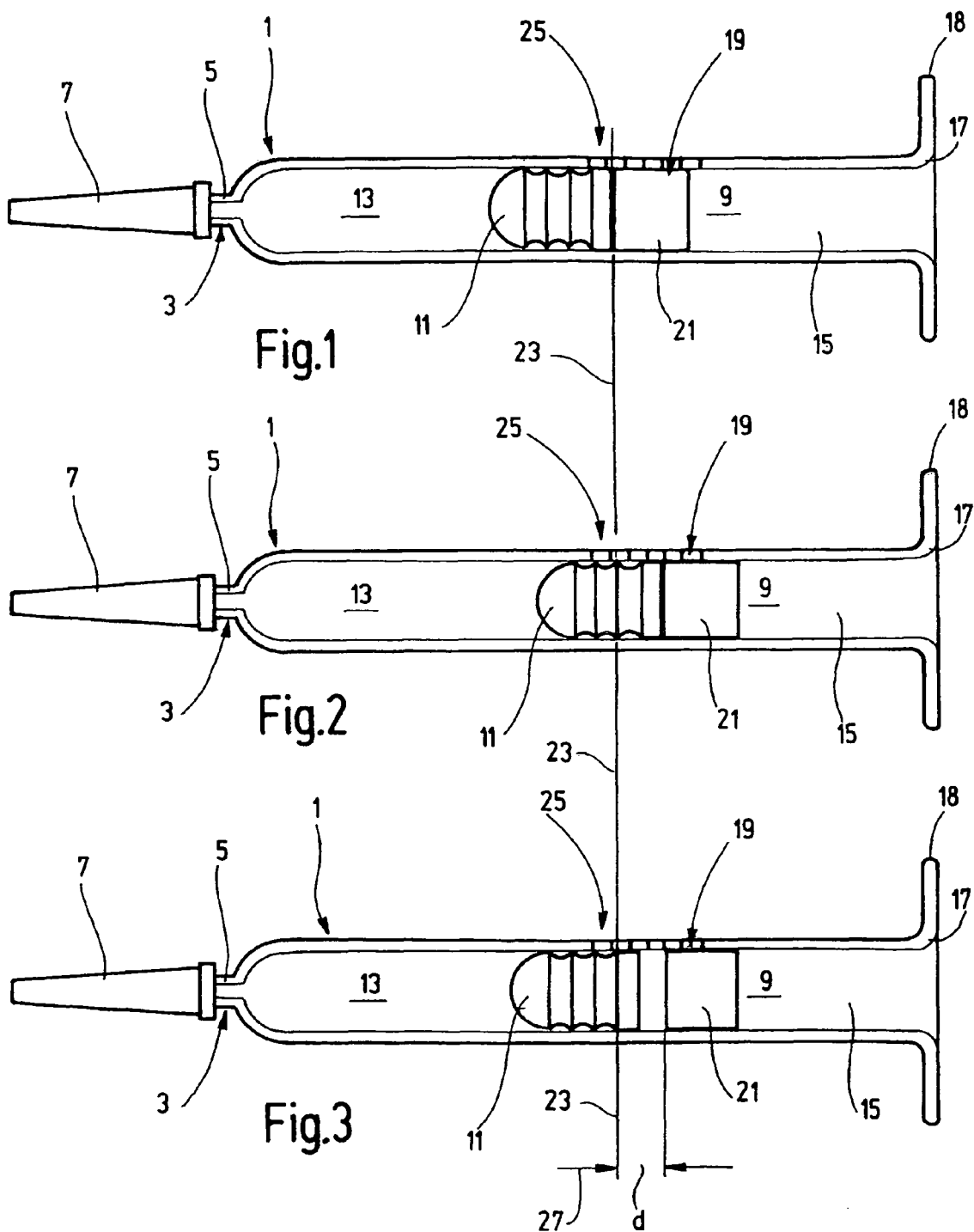

SYRINGE CYLINDER

CROSS-REFERENCE TO RELATED APPLICATIONS

Figure 4:
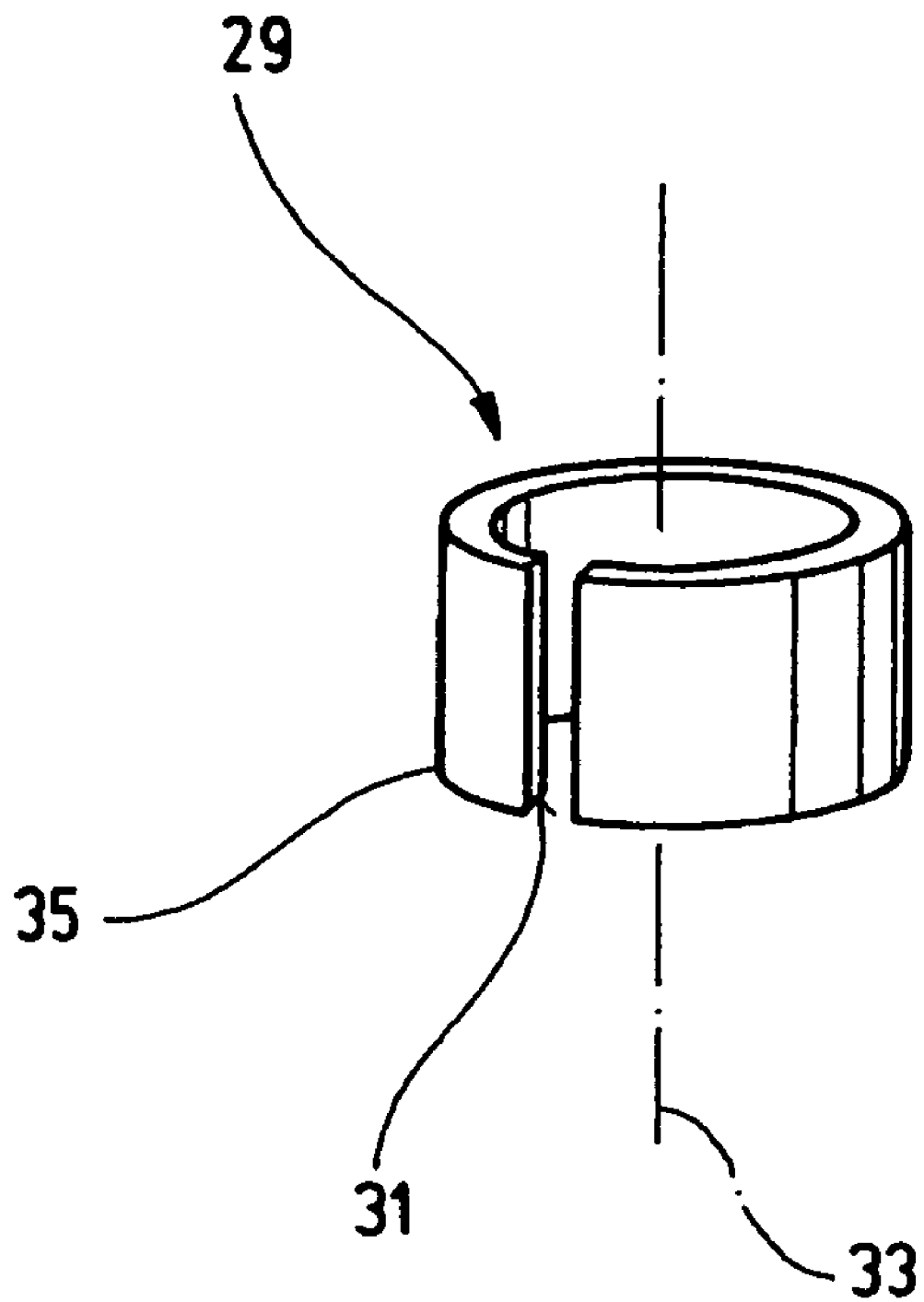

This application is a 371 U.S. National Stage of International Application No. PCT/EP2007/003429, filed Apr. 19, 2007. This application claims priority to German Patent Application No. 10 2006 018 651.6, filed Apr. 21, 2006, the disclosures of which are incorporated herein by reference.

FIELD

The invention relates to a syringe cylinder having an interior space according to the preamble of claim 1.

BACKGROUND

Syringe cylinders of the kind in question here are known. They have an interior space comprising a stopper, which delimits an active ingredient space toward the outside. The active ingredient space may comprise an air bubble, which can expand and contract during temperature fluctuations, and particularly during pressure fluctuations, during air transport of the syringe cylinder. Due to pressure differences, the stopper in the interior space of the syringe cylinder may be displaced. In this process, it may reach regions of the interior space that are not, or not sufficiently, sterile. During a return displacement of the stopper due to a change in temperature, or in the event of a pressure drop, the active ingredient space may thus become contaminated. In order to be able to determine whether the stopper has been shifted beyond a maximum permitted range before employing a syringe cylinder, and before using a drug accommodated in the active ingredient space, it is necessary to determine the range traveled by the stopper. It is known to provide the interior space of a syringe cylinder on the side of a stopper facing away from the active ingredient space with graphite powder. The graphite powder adhering to the inside wall of the syringe cylinder is shifted as the stopper is displaced, so that upon a return displacement of the stopper a powder-free region of the inside wall of the syringe cylinder becomes visible. In order to be able to detect a displacement of the stopper, for example during air transport, in conventional syringe cylinders the region free from graphite powder has been determined. Starting with a certain width of this region, measured in the longitudinal direction of the syringe cylinder, it was safe to assume that the stopper had reached regions of the interior space that were not, or not sufficiently, sterilized and that the active ingredient space could be contaminated. It was then possible to sort such syringe cylinders.

It has been shown that the friction forces between the stopper and inside wall of the syringe cylinder were modified by the graphite powder. This possibly resulted in falsified measurement results. In addition, the graphite powder was able to travel back to the region over which the stopper passed during a shift. As a result, it was not detectable with certainty whether a stopper in fact had reached non-sterile regions or not.

SUMMARY

It is therefore the aim of the invention to provide a syringe cylinder, in which the displacement path of the stopper can be biuniquely identified.

In order to achieve this aim, a syringe cylinder is proposed, which has an interior space comprising a stopper, which separates a region of the interior space in which an active ingredient has been introduced. In this way, an active ingredient space is created, which is sealed relative to the environment by the stopper. The syringe cylinder is characterized in that an indicator device is provided. This device is intended to biuniquely indicate a longitudinal movement of the stopper performed in one direction inside the interior space. If the stopper should have moved away from the active ingredient space due to temperature, or particularly pressure fluctuations, the indicator device biuniquely indicates the displacement travel. Therefore, even if the stopper displaced back, the displacement travel is always clearly detectable for quality control of the syringe cylinder.

A particularly preferred embodiment of the syringe cylinder is characterized in that the indicator device comprises an indicator element. This element is disposed movably in the interior space of the syringe cylinder and configured such that the outside diameter thereof is adapted to the inside diameter of the interior space. In addition, the material pairing of the material used for the syringe cylinder and that for the indicator element is matched. This is necessary in order to build friction forces between the indicator element and the inside wall of the syringe cylinder. These are configured such that, upon a displacement of the stopper in the interior space of the syringe cylinder, the indicator element can be displaced by the stopper in one direction, which is to say in a direction leading away from the active ingredient space. If the active ingredient space undergoes a plurality of temperature or pressure fluctuations, the stopper can move away from the active ingredients space accordingly a number of times, displacing the indicator element in the process. The stopper is not coupled to the indicator element, so that during a return displacement of the same the indicator element is held in a position by the friction forces, once said position has been assumed. During a return displacement of the stopper, the indicator element thus remains fixed in the position thereof in the interior space of the syringe cylinder. As a result, the maximum displacement of the stopper can be biuniquely identified based on the position of the indicator element.

Further embodiments will be apparent from the subordinate claims.

DRAWINGS

The invention will be explained in more detail below with reference to the attached figures, wherein:

FIGS. 1 to 3 are schematic diagrams of a syringe cylinder in partial longitudinal sections, and FIG. 4 shows an indicator element in a perspective view.

DETAILED DESCRIPTION

FIG. 1 shows a longitudinal section of a syringe cylinder 1. It has a first end 3, comprising a needle projection 5 onto which a cap 7 is placed.

The interior space 9 of the syringe cylinder 1 is divided into two regions by a stopper 11 displaceable in the longitudinal direction of the syringe cylinder 1: To the left of the stopper 11, a closed region is provided, into which an active ingredient can be introduced, and which hereinafter is therefore referred to as the active ingredient space 13. To the right of the stopper 11, a space 15 is provided, which is open relative to the environment and is therefore not sterile.

On the second end 17 of the syringe cylinder 1, this end being located opposite the first end 3, a protrusion is provided, which can serve as a finger support 18 or for attaching a finger support 18.

The syringe cylinder 1 comprises an indicator device 19, which in the example shown encompasses an indicator element 21. This element is accommodated on the side of the stopper 11 facing away from the active ingredient space 13 in the space 15 and can be displaced in this space in the longitudinal direction of the syringe cylinder 1.

The outside diameter of the indicator element 21 is matched to the inside diameter of the space 15 that it can only be displaced in the interior space 9 when overcoming a certain friction force. In FIG. 1, the stopper 11 is in a starting position, which it assumes, for example, after filling the active ingredient space 13 under atmospheric pressure. This position is indicated by an auxiliary line 23 shown perpendicular to the longitudinal extension of the syringe cylinder 1, the right end of the stopper 11 resting against this line, and also the left end of the indicator element 21. The stopper 11 and the indicator element 21 thus preferably rest against each other in the starting situation. FIG. 1 also indicates that the syringe cylinder 1 comprises a measuring device, preferably a scale 25.

FIG. 2 shows the syringe cylinder 1 illustrated in FIG. 1. Identical parts are identified with identical reference numerals, so that in this respect only reference is made to the description of FIG. 1.

The only difference to the illustration according to FIG. 1 is that the stopper 11 was displaced to the right compared to FIG. 1. The right end of the stopper 11 thus is located to the right of the auxiliary line 23.

Since the indicator element 21 rested against the stopper 11 in the starting position according to FIG. 1, during a displacement of the stopper 11 to the right beyond the auxiliary line 23 the element is likewise moved to the right by overcoming the friction forces between the indicator element 21 and the inside wall of the syringe cylinder 1.

A displacement of the stopper 11 to the right may occur in that the temperature in the active ingredient space 13 is increased, so that overpressure is created there; on the other hand, it can particularly occur in that the syringe cylinder 1 is introduced in a region, the pressure of which is below atmospheric pressure. This occurs, for example, during air transport of the syringe cylinder 1. Due to the resulting overpressure in the active ingredient space 13, the stopper 11 is then displaced to the right relative to the auxiliary line 23, as is apparent from FIG. 2.

FIG. 3 shows the syringe cylinder 1 having a stopper 11 that has been displaced back. Parts agreeing with those according to FIGS. 1 and 2 are denoted with identical reference numerals, so that in this respect reference is made to the described above in order to avoid repetitions.

In FIG. 3, the stopper 11 is shifted to the left compared to the position shown in FIG. 2. Since it is designed such that it can only be displaced when overcoming friction forces in the inside of the syringe cylinder 1, it will not return to the starting position shown in FIG. 1, even if the syringe cylinder 1 is under atmospheric pressure. This is apparent in that it is still displaced slightly to the right relative to the auxiliary line 23, however not as far as is shown in FIG. 2.

Since the indicator element 21 can only be displaced when overcoming friction forces in the interior space 9 of the syringe cylinder 1 and is not coupled to the stopper 11, the element remains in the position shown in FIG. 2, even if, as shown in FIG. 3, the stopper 11 is displaced back to the left in the direction of the first end 3 of the syringe cylinder 1.

The following describes the function of the indicator device 19 of the syringe cylinder 1 in more detail:

In connection with FIGS. 1 to 3, it became apparent that the stopper 11 can be displaced out of a starting position according to FIG. 1, which is marked with the auxiliary line 23. If overpressure is present in the active ingredient space 13 relative to a pressure in the space 15, the stopper 11 is displaced to the right relative to the auxiliary line 23 as soon as the friction forces between the stopper 11 and the inside wall of the syringe cylinder 1 are overcome. During a displacement to the right, as is shown in FIG. 2, the indicator element 21 of the indicator device 19 is also displaced to the right, which in the starting position according to FIG. 1 already rests against the right side of the stopper 11, which is to say against the side facing away from the active ingredient space 13. The friction forces between the indicator element 21 and the inside wall of the syringe cylinder 1 are so low that a displacement of the indicator element 21 to the right beyond the auxiliary line 23 is possible by the force of the stopper 11. On the other hand, the friction forces are so high that the indicator element 21, which is not coupled to the stopper 11, does not move back to the left out of the position shown in FIG. 2 if the stopper 11 is displaced back to the left relative to the auxiliary line 23 according to FIG. 3.

A double arrow indicates that the left edge of the indicator element 21 remains disposed at a distance d from the auxiliary line 23, even if the stopper is displaced back.

The distance d can be determined based on the scale 25.

In principle, with syringe cylinder of the type described here, a first zone is defined, which is associated with the active ingredient space 13 and is sterile after filling the syringe cylinder 1. If the stopper 11 is displaced to the right beyond this zone, which is to say relative to the auxiliary line 23 shown in this example, it finally reaches regions in which the interior space 9 of the syringe cylinder 1 is no longer stable. During a return displacement of the stopper 11, the active ingredient in the active ingredient space 13 can become contaminated.

Thus, if the stopper 11 is displaced to the right beyond a defined distance d, which is indicated biuniquely by the indicator element 21, a user can discard the syringe cylinder 1 in order to avoid putting a patient at risk.

Since, due to the friction forces in relation to the inside wall of the syringe cylinder 1, the indicator element 21 is not displaced back out of the position thereof assumed in FIG. 2, which is apparent from FIG. 3, the maximum displacement of the stopper 11 to the right beyond the auxiliary line 23 can be indicated biuniquely.

It is apparent from the explanations for FIGS. 1 to 3 that for the basic function of the indicator device 19 the specific configuration of the indicator element 21 plays a subordinate role: The only crucial aspect is that the indicator element 21 can be displaced in the interior space 9 of the syringe cylinder 1 during a displacement of the stopper 11 in one direction, which is to say to the right beyond the auxiliary line 23. During a movement of the stopper 11 in the opposite direction, the indicator element 21, however, is supposed to remain in a position, once reached, as a result of the friction forces so that the maximum displacement of the stopper 11 always remains clearly identifiable.

One embodiment of the indicator element 21 is shown in FIG. 4. The figure shows an indicator element configured as a ring 29, which preferably has a slot 31 extending in the longitudinal direction of the syringe cylinder 1. This increases the elasticity of the ring 29. The outside diameter, in the relaxed state, is slightly larger than the inside diameter of the interior space 9 of the syringe cylinder. Thus, if the ring 29 is inserted in the interior space 9, it is slightly compressed, so that friction forces build between the inside wall of the interior space 9 and the outside surface of the ring 29.

The friction forces can be adjusted, for example, by the selection of the material of the ring 29. It may, for example, comprise Teflon on the circumferential surface thereof, or be made of this material. The material of the indicator element 21 is matched to the material of the syringe cylinder 1, which can be made of glass, plastic, or the like.

In order to adjust the friction forces, it is also possible to provide ribs on the circumferential surface of the ring 29 extending on the circumferential surface or in the longitudinal direction of the syringe cylinder 1. The ribs can be made of a different material than the base body of the ring 29.

The friction forces can also be adjusted in that the thickness of the ring 29 and the width of the slot 31 are varied.

Finally, it is also possible to provide one or more lips 35 on the outside surface of the ring 29, the lips being inclined at an angle relative to the center line 33 of the ring 29 and enclosing an angle α with the center line 33, the angle—as is shown in FIGS. 1 to 3—opening in the direction of the stopper 11. During a displacement of the ring 29 according to FIG. 2 such a lip 35 is located to the right. If the ring 29 were to be moved to the left, the lip 35 would be shored up and counteract such a movement.

In addition, it has been shown that the indicator element 21 can also have different basic shapes, particularly if it is removed before attaching a piston rod to the stopper 11. For example, a web extending along a diameter line may be provided, the longitudinal edges of which build a certain friction force with the inside wall of the syringe cylinder 1. It is also possible to use Y, X or star-shaped bodies as the indicator element and accommodate them in the interior space 9.

In a particularly preferred embodiment, the indicator element explained with reference to FIG. 4 is used, because as a result of the free space enclosed by the ring 29 a piston rod can be introduced into the interior space 9, particularly the space 15, and screwed into the stopper 11. This does not impair the mobility of the ring 29, particularly if the outside diameter of the piston rod is smaller than the inside diameter of the ring 29.

Overall, it becomes apparent that the syringe cylinder 1 is characterized by the specially configured indicator device 19, the indicator element 21 of which can be exclusively displaced in one direction by the stopper 11 and remains in a position once reached, in order to biuniquely indicate the displacement of the stopper 11, even if the stopper has been displaced back.

From the explanations regarding FIGS. 1 to 3, it became apparent that the distance d between the edge of the indicator element 21 facing the active ingredient space 13 and the auxiliary line 23 can be read based on the scale 25. This can be performed by means of an optical reading device, be it by means of a camera, a microscope, or the like.

The reading of the maximum displacement of the indicator element 21, however, can also be performed by means of an aperture: It is possible to provide the syringe cylinder 1 with a bar or ring extending the cylinder longitudinal direction, the bar or ring being opaque. The length of the bar or ring measured in the axial direction of the syringe cylinder 1 corresponds to the maximum permitted distance d by which the indicator element 21 may be displaced during a shift of the stopper 11. The edge of the indicator element 21 facing the active ingredient space 13 is covered by the bar or the ring if during a displacement of the indicator element 21 the maximum distance d is not exceeded. However, if this is the case, a gap becomes visible between the edge of the indicator element 21 facing the active ingredient space 13 and the edge of the bar or ring facing away from the active ingredient space, the gap biuniquely indicating the inadmissible displacement of the stopper 11, or of the indicator element 21.

The invention claimed is:

1. A syringe cylinder comprising:
 a body defining an interior space;
 a stopper displaceably disposed relative to the body, the stopper delimiting an active ingredient space and;
 an indicator device delimited by the stopper, the indicator device indicating a longitudinal movement of the stopper occurring in a direction away from the active ingredient, the indicator device including an indicator element, the indicator element movable in the interior space of the syringe cylinder against a friction force, the friction force being such that, if over pressure is present in the active ingredient space independent of any user applied force, the stopper can be displaced with the indicator element in the longitudinal direction of the syringe cylinder away from the active ingredient, and that the indicator element remains fixed in the position thereof in the interior space during a return displacement of the stopper.

2. The syringe cylinder according to claim 1 wherein the indicator device is configured as a ring, the ring preferably having a slot.

3. The syringe cylinder according to claim 1 wherein the indicator device has at least one web, a width of the web corresponding substantially to an inside diameter of the interior space.

4. The syringe cylinder according to claim 3, wherein the indicator element is configured as a cross having at least three webs.

5. The syringe cylinder according to claim 1, further comprising a measuring device depicting a displacement of the indicator element relative to the stopper.

6. The syringe cylinder according to claim 5, wherein the measuring device is a scale.

7. The syringe cylinder according to claim 5, wherein the measuring device is an aperture.

8. The syringe cylinder according to claim 1, wherein the indicator element abuts but is unconnected to the stopper.

9. The syringe cylinder according to claim 1, wherein the indicator element is displaceable by the stopper in a first direction away from the active ingredient but unaffected by movement in a second direction, the second direction being opposite the first direction.

10. A syringe cylinder comprising:
 a body defining an interior space;
 a stopper displaceably disposed in the interior space;
 an active ingredient disposed in the interior space on a first side of the stopper; and
 an indicator device disposed on a second side of the stopper, the second side being opposite the first side, the indicator element abutting but unconnected to the stopper and functionally held in place within the interior space unless displaced by the stopper in a direction away from the active ingredient caused by overpressure in the interior space holding the active ingredient, wherein the overpressure is due to changes in pressure in the interior space holding the active ingredient and independent from any user applied force on the stopper;
 wherein the indicator element is displaceable by the stopper in a first direction away from the active ingredient but unaffected by movement in a second direction, the second direction being opposite the first direction.

* * * * *